(12) United States Patent
Hwang

(10) Patent No.: US 7,537,581 B2
(45) Date of Patent: May 26, 2009

(54) NEEDLE SHIELD ASSEMBLY HAVING HINGED NEEDLE SHIELD AND FLEXIBLE CANNULA LOCK

(75) Inventor: Charles G. Hwang, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 356 days.

(21) Appl. No.: 11/609,441

(22) Filed: Dec. 12, 2006

(65) Prior Publication Data

US 2007/0106224 A1 May 10, 2007

Related U.S. Application Data

(63) Continuation of application No. 10/488,811, filed as application No. PCT/US02/20333 on Jun. 27, 2002, now abandoned.

(60) Provisional application No. 60/303,940, filed on Jul. 9, 2001.

(51) Int. Cl.
*A61M 5/00* (2006.01)
*A61M 5/32* (2006.01)

(52) U.S. Cl. .................. 604/110; 604/192; 604/263

(58) Field of Classification Search ................ 604/263, 604/192, 110, 198, 187, 158, 171, 160–163, 604/164.08, 197
See application file for complete search history.

(56) References Cited

U.S. PATENT DOCUMENTS

| 1,779,451 | A | 10/1930 | Sponsel |
| 2,004,050 | A | 6/1935 | Kerk |
| 2,700,385 | A | 1/1955 | Ortiz |
| 2,836,942 | A | 6/1958 | Miskel |
| 2,854,976 | A | 10/1958 | Heydrich |
| 2,953,243 | A | 9/1960 | Roehr |
| 3,021,942 | A | 2/1962 | Hamilton |
| 3,073,307 | A | 1/1963 | Stevens |
| 3,074,542 | A | 1/1963 | Myerson et al. |
| 3,255,873 | A | 6/1966 | Speelman |
| 3,294,231 | A | 12/1966 | Vanderbeck |
| 3,323,523 | A | 6/1967 | Scislowicz et al. |
| 3,329,146 | A | 7/1967 | Waldman, Jr. |
| 3,333,682 | A | 8/1967 | Burke |
| 3,367,488 | A | 2/1968 | Hamilton |
| 3,485,239 | A | 12/1969 | Vanderbeck |

(Continued)

FOREIGN PATENT DOCUMENTS

GB 1233302 5/1971

(Continued)

*Primary Examiner*—Nicholas D Lucchesi
*Assistant Examiner*—Rebecca E Eisenberg

(57) ABSTRACT

A needle shield and needle shield assembly are provided for preventing accidental needle sticks. The needle shield includes opposing sidewalls and is pivotable between an open position that allows use of the needle cannula and a closed position that covers at least the tip of the needle cannula. A locking member extends from one of the sidewalls of the needle shield and includes a relatively rigid base portion and a relatively flexible end portion. The needle cannula engages the relatively flexible end portion when entering the needle shield cavity, deflecting it with respect to the base portion. Upon any attempt to move the needle shield from the closed position to the open position, the needle cannula is directed by the locking member towards the relatively rigid base portion, thereby making it very difficult to reuse the needle cannula.

19 Claims, 10 Drawing Sheets

U.S. PATENT DOCUMENTS

| | | |
|---|---|---|
| 3,537,452 A | 11/1970 | Wilks |
| 3,610,240 A | 10/1971 | Harautuneian |
| 3,658,061 A | 4/1972 | Hall |
| 3,828,775 A | 8/1974 | Armel |
| 3,890,971 A | 6/1975 | Leeson et al. |
| 3,904,033 A | 9/1975 | Haerr |
| 3,934,722 A | 1/1976 | Goldberg |
| 3,968,876 A | 7/1976 | Brookfield |
| 4,113,090 A | 9/1978 | Carstens |
| 4,139,009 A | 2/1979 | Alvarez |
| 4,175,008 A | 11/1979 | White |
| 4,300,678 A | 11/1981 | Gyure et al. |
| RE31,086 E | 11/1982 | Johnson, Jr. et al. |
| 4,375,849 A | 3/1983 | Hanifl |
| 4,430,082 A | 2/1984 | Schwabacher |
| 4,592,744 A | 6/1986 | Jagger et al. |
| 4,634,428 A | 1/1987 | Cuu |
| 4,643,722 A | 2/1987 | Smith, Jr. |
| 4,659,330 A | 4/1987 | Nelson et al. |
| 4,664,249 A | 5/1987 | Gherardi |
| 4,664,259 A | 5/1987 | Landis |
| 4,664,654 A | 5/1987 | Strauss |
| 4,671,408 A | 6/1987 | Raines et al. |
| 4,681,567 A | 7/1987 | Masters et al. |
| 4,695,274 A | 9/1987 | Fox |
| 4,702,738 A | 10/1987 | Spencer |
| 4,723,943 A | 2/1988 | Spencer |
| 4,728,320 A | 3/1988 | Chen |
| 4,728,321 A | 3/1988 | Chen |
| 4,731,059 A | 3/1988 | Wanderer et al. |
| 4,735,311 A | 4/1988 | Lowe et al. |
| 4,735,618 A | 4/1988 | Hagen |
| 4,737,144 A | 4/1988 | Choksi |
| 4,738,663 A | 4/1988 | Bogan |
| 4,743,233 A | 5/1988 | Schneider |
| 4,746,008 A | 5/1988 | Heverly et al. |
| 4,747,836 A | 5/1988 | Luther |
| 4,747,837 A | 5/1988 | Hauck |
| 4,772,272 A | 9/1988 | McFarland |
| 4,778,453 A | 10/1988 | Lopez |
| 4,781,697 A | 11/1988 | Slaughter |
| 4,782,841 A | 11/1988 | Lopez |
| 4,790,828 A | 12/1988 | Dombrowski et al. |
| 4,793,484 A | 12/1988 | Schoettle |
| 4,795,432 A | 1/1989 | Karczmer |
| 4,795,443 A | 1/1989 | Permenter et al. |
| 4,801,295 A | 1/1989 | Spencer |
| 4,804,372 A | 2/1989 | Laico et al. |
| 4,813,426 A | 3/1989 | Haber et al. |
| 4,816,022 A | 3/1989 | Poncy |
| 4,816,024 A | 3/1989 | Sitar et al. |
| 4,819,659 A | 4/1989 | Sitar |
| 4,820,277 A | 4/1989 | Norelli |
| 4,826,490 A | 5/1989 | Byrne et al. |
| 4,826,491 A | 5/1989 | Schramm |
| 4,838,871 A | 6/1989 | Luther |
| 4,842,587 A | 6/1989 | Poncy |
| 4,846,796 A | 7/1989 | Carrell et al. |
| 4,850,968 A | 7/1989 | Romano |
| 4,850,976 A | 7/1989 | Heinrich et al. |
| 4,850,977 A | 7/1989 | Bayless |
| 4,850,978 A | 7/1989 | Dudar et al. |
| 4,850,994 A | 7/1989 | Zerbst et al. |
| 4,850,996 A | 7/1989 | Cree |
| 4,858,607 A | 8/1989 | Jordan et al. |
| 4,863,434 A | 9/1989 | Bayless |
| 4,863,435 A | 9/1989 | Sturman et al. |
| 4,863,436 A | 9/1989 | Glick |
| 4,867,746 A | 9/1989 | Dufresne |
| 4,872,552 A | 10/1989 | Unger |
| 4,874,383 A | 10/1989 | McNaughton |
| 4,874,384 A | 10/1989 | Nunez |
| 4,883,469 A | 11/1989 | Glazier |
| 4,886,503 A | 12/1989 | Miller |
| 4,888,001 A | 12/1989 | Schoenberg |
| 4,892,107 A | 1/1990 | Haber |
| 4,892,521 A | 1/1990 | Laico et al. |
| 4,900,309 A | 2/1990 | Netherton et al. |
| 4,909,791 A | 3/1990 | Norelli |
| 4,909,792 A | 3/1990 | Norelli |
| 4,921,096 A | 5/1990 | McFarlane |
| 4,927,018 A | 5/1990 | Yang et al. |
| 4,944,397 A | 7/1990 | Miller |
| 4,944,731 A | 7/1990 | Cole |
| 4,966,591 A | 10/1990 | Yuen |
| 4,976,699 A | 12/1990 | Gold |
| 4,982,842 A | 1/1991 | Hollister |
| 5,011,475 A | 4/1991 | Olson |
| 5,011,479 A | 4/1991 | Le et al. |
| 5,017,189 A * | 5/1991 | Boumendil .................. 604/192 |
| 5,055,102 A | 10/1991 | Sitnik |
| 5,078,693 A | 1/1992 | Shine |
| 5,116,325 A | 5/1992 | Paterson |
| 5,135,509 A | 8/1992 | Olliffe |
| 5,139,489 A | 8/1992 | Hollister |
| 5,151,089 A | 9/1992 | Kirk, III et al. |
| 5,154,285 A | 10/1992 | Hollister |
| 5,188,611 A | 2/1993 | Orgain |
| 5,197,954 A | 3/1993 | Cameron |
| 5,207,653 A | 5/1993 | Janjua et al. |
| 5,232,454 A | 8/1993 | Hollister |
| 5,232,455 A | 8/1993 | Hollister |
| 5,242,417 A | 9/1993 | Paudler |
| 5,277,311 A | 1/1994 | Hollister |
| 5,312,369 A | 5/1994 | Arcusin et al. |
| 5,401,251 A | 3/1995 | Hui |
| 5,405,332 A | 4/1995 | Opalek |
| 5,423,765 A | 6/1995 | Hollister |
| 5,462,534 A | 10/1995 | Debreczeni |
| 5,485,854 A | 1/1996 | Hollister |
| 5,486,163 A | 1/1996 | Haynes |
| 5,490,841 A | 2/1996 | Landis |
| 5,509,907 A | 4/1996 | Bevilacqua |
| 5,533,984 A | 7/1996 | Parmigiani |
| 5,584,816 A | 12/1996 | Gyure et al. |
| 5,599,313 A | 2/1997 | Gyure et al. |
| 5,599,318 A | 2/1997 | Sweeney et al. |
| 5,603,699 A | 2/1997 | Shine |
| 5,632,732 A | 5/1997 | Szabo et al. |
| 5,643,219 A | 7/1997 | Burns |
| 5,662,617 A | 9/1997 | Odell et al. |
| 5,665,075 A | 9/1997 | Gyure et al. |
| 5,669,889 A | 9/1997 | Gyure et al. |
| 5,681,295 A | 10/1997 | Gyure et al. |
| 5,693,022 A | 12/1997 | Haynes |
| 5,702,369 A | 12/1997 | Mercereau |
| 5,733,265 A | 3/1998 | Bachman et al. |
| 5,735,827 A * | 4/1998 | Adwers et al. .............. 604/263 |
| 5,746,726 A | 5/1998 | Sweeney et al. |
| 5,807,351 A | 9/1998 | Kashmer |
| 5,836,920 A | 11/1998 | Robertson |
| 5,868,716 A | 2/1999 | Sweeney et al. |
| 5,876,831 A | 3/1999 | Rawal |
| 5,885,249 A | 3/1999 | Irisawa |
| 5,910,130 A | 6/1999 | Caizza et al. |
| 5,913,846 A | 6/1999 | Szabo |
| 5,993,426 A | 11/1999 | Hollister |
| 6,077,253 A | 6/2000 | Cosme |
| 6,080,137 A | 6/2000 | Pike |
| 6,120,482 A | 9/2000 | Szabo |
| 6,139,533 A | 10/2000 | Xia et al. |
| RE37,110 E | 3/2001 | Hollister |
| RE37,252 E | 7/2001 | Hollister |
| 6,319,232 B1 | 11/2001 | Kashmer |

| | | | | | |
|---|---|---|---|---|---|
| 6,328,713 B1 | 12/2001 | Hollister | GB | 2239607 | 7/1991 |
| 6,334,857 B1 | 1/2002 | Hollister et al. | GB | 2240273 | 7/1991 |
| 6,699,217 B2 | 3/2004 | Bennett et al. | GB | 2240477 | 8/1991 |
| 2004/0215154 A1 | 10/2004 | Hwang et al. | WO | WO 87/07162 | 12/1987 |
| 2005/0054986 A1 | 3/2005 | Simpson et al. | WO | WO 90/01348 | 2/1990 |
| 2005/0065481 A1 | 3/2005 | Hauri et al. | WO | WO 91/09637 | 7/1991 |
| 2005/0065482 A1 | 3/2005 | Hauri et al. | WO | WO 91/09638 | 7/1991 |
| | | | WO | WO 91/09639 | 7/1991 |
| | FOREIGN PATENT DOCUMENTS | | WO | WO 93/16745 | 9/1993 |
| GB | 2239604 | 7/1991 | * cited by examiner | | |

NEEDLE SHIELD ASSEMBLY HAVING HINGED NEEDLE SHIELD AND FLEXIBLE CANNULA LOCK

This application is a continuation of U.S. application Ser. No. 10/488,881, which was filed on Mar. 4, 2004, which claims the benefit of International (PCT) Application No. PCT/US02/20333, filed Jun. 27, 2002, which claims benefit of U.S. Provisional Application No. 60/303,940 filed Jul. 9, 2001.

FIELD OF THE INVENTION

The field of the invention relates to needle shield assemblies for medical devices such as hypodermic needles.

BACKGROUND OF THE INVENTION

Accidental needle sticks from used hypodermic needles can transmit disease. Accordingly, various types of needle shields have been designed to reduce the possibility of accidental sticks.

A needle shield that is hinged near the base of the needle has the advantage of allowing one handed needle reshielding. A number of prior art needle shield assemblies including such needle shields have been developed.

Various means have been provided for locking a hinged needle shield in the closed (needle protecting) position. Deflectable members have been provided in the needle shield for engaging the needle upon shielding and preventing subsequent unshielding of the needle. Such members trap the needle within the needle shield. U.S. Pat. No. 4,664,259 discloses a needle shield including a deflectable member. Locking has also been accomplished by locking engagement of the needle shield with the needle support structure. U.S. Pat. No. 5,746,726 discloses a shielded needle assembly of this type.

Needles are available in a number of gauges and lengths so that they can be used for different purposes. Where a needle shield having a deflectable locking member is used to entrap a needle, it is important that the needle displace the locking member or members as it enters the needle shield cavity. It is also important that, since the needle is entrapped by the deflectable locking member or members, it cannot easily be displaced from the cavity. A relatively large diameter needle can more easily displace a deflectable locking member than a small diameter needle, both entering the needle shield cavity and exiting the cavity. As a needle shield should preferably be usable to protect needles of various sizes, the deflectable locking member or members should be designed such that it is sufficiently flexible to allow even a relatively small diameter needle to deflect it as it enters the needle shield cavity, but provides sufficient resistance to prevent the needle from being re-exposed through the opening of the cavity.

U.S. Pat. No. 5,486,163 discloses a sheath that is described as requiring very little force to open a pair of inwardly biased doors as the needle enters the cavity and a much greater force to open them outwardly to expose the needle. Other needle sheaths have deflectable members in the form of hooks, as shown in U.S. Pat. Nos. 4,664,259, 4,944,731, 5,139,489, 5,681,295 and 5,876,381. Still other sheaths include deflectable members integral with a sidewall thereof and extending away from the cavity opening. U.S. Pat. No. 5,490,841 discloses such a sheath wherein the needle is caused to travel towards the resilient hinge of a deflectable member if one attempts to re-expose it. The free end of the deflectable member engages the opposing sidewall of the sheath to prevent it from opening and thereby allowing release of the needle.

SUMMARY OF THE INVENTION

A needle shield assembly of the present invention includes a needle cannula having a proximal end, a distal end and a lumen therethrough. A hub is provided having a proximal end for connecting to a medical device such as a syringe and a distal end connected to the proximal end of the needle cannula. A base member is connected to or integral with the hub. A needle shield is coupled to the base member by a hinge. A locking assembly having one or more locking members for engaging the needle cannula is provided. The locking member includes an end portion and a base portion. The end portion is relatively flexible while the base portion is relatively stiff. The shaft of a needle cannula can accordingly deflect the end portion of the locking member relatively easily upon entering the needle shield cavity. If the needle shield is pivoted in an attempt to re-expose the trapped needle cannula, the shaft of the needle cannula will engage the more rigid base portion of the locking member.

In accordance with one embodiment of the invention, a needle shield is provided which includes a proximal end portion, a distal end portion and a needle cannula locking member. The proximal end portion includes a connector while the distal end portion defines an elongate cavity for enveloping at least part of a needle cannula and an elongate cavity opening. The needle cannula locking member is coupled to the distal end portion and extends away from the elongate cavity opening and into the elongate cavity. The locking member includes a relatively rigid base portion and a plurality of relatively flexible end portions coupled to the base portion.

A needle shield assembly according to the invention includes a needle cannula having a proximal end, a distal and a lumen therethrough. It further includes a needle support wherein the needle cannula is connected to the needle support. A needle shield is hingedly connected to the needle support and includes an elongate cavity, a pair of opposing sidewalls bordering the cavity, and a cavity opening. A locking member is connected to one of the sidewalls and extends into the elongate cavity away from the cavity opening. The locking member includes a base portion adjoining one of the side walls, a flexible end portion adjoining the base portion, and inner and outer surfaces that converge in the direction away from one of the side walls. The end portion of the locking member is relatively flexible with respect to the base portion. The flexible end portion is deflectable with respect to the base portion by the needle cannula as the needle shield is moved towards a closed position to protect the needle cannula. If one attempts to move the needle shield from the closed position to the open position, the needle cannula is directed towards one of the sidewalls by the inner surface of the locking member. The needle cannula is accordingly directed towards the base portion of the locking member.

The invention is further directed to a medical device such as a syringe assembly. The device includes a vessel having a first end and a second end. A needle cannula is connected to the first end of the vessel, and includes a proximal end, a distal end and a lumen therethrough. A needle shield is pivotably coupled to the vessel and includes first and second opposing sidewalls, a cavity between the sidewalls for receiving at least part of the needle cannula, and a cavity opening. The needle shield is pivotable between an open position where at least the distal end of the needle cannula is exposed and a closed position where at least the distal end of the needle cannula is positioned within the cavity. A locking member is connected to the first sidewall of the needle shield and extends away from the cavity opening and into the cavity. It includes a relatively rigid base portion adjoining the first sidewall and a relatively flexible end portion extending from the base portion and defining a free end. The locking member is positioned such that the needle cannula contacts and displaces the relatively flexible end portion upon movement of the needle shield into the closed position. The locking member further includes an outer surface opposing the cavity opening and an inner surface extending at an acute angle with respect to the first sidewall of the needle shield. When the needle shield is moved from the closed position towards the open position, the needle cannula is accordingly urged by the inner surface of the locking member towards the first sidewall. The medical device of this embodiment may include a plurality of relatively flexible end portions. The end portion may be long enough to be flexed so that the free end contacts the second sidewall to help prevent the needle from leaving the shield cavity.

DETAILED DESCRIPTION OF THE INVENTION

Figure 1:
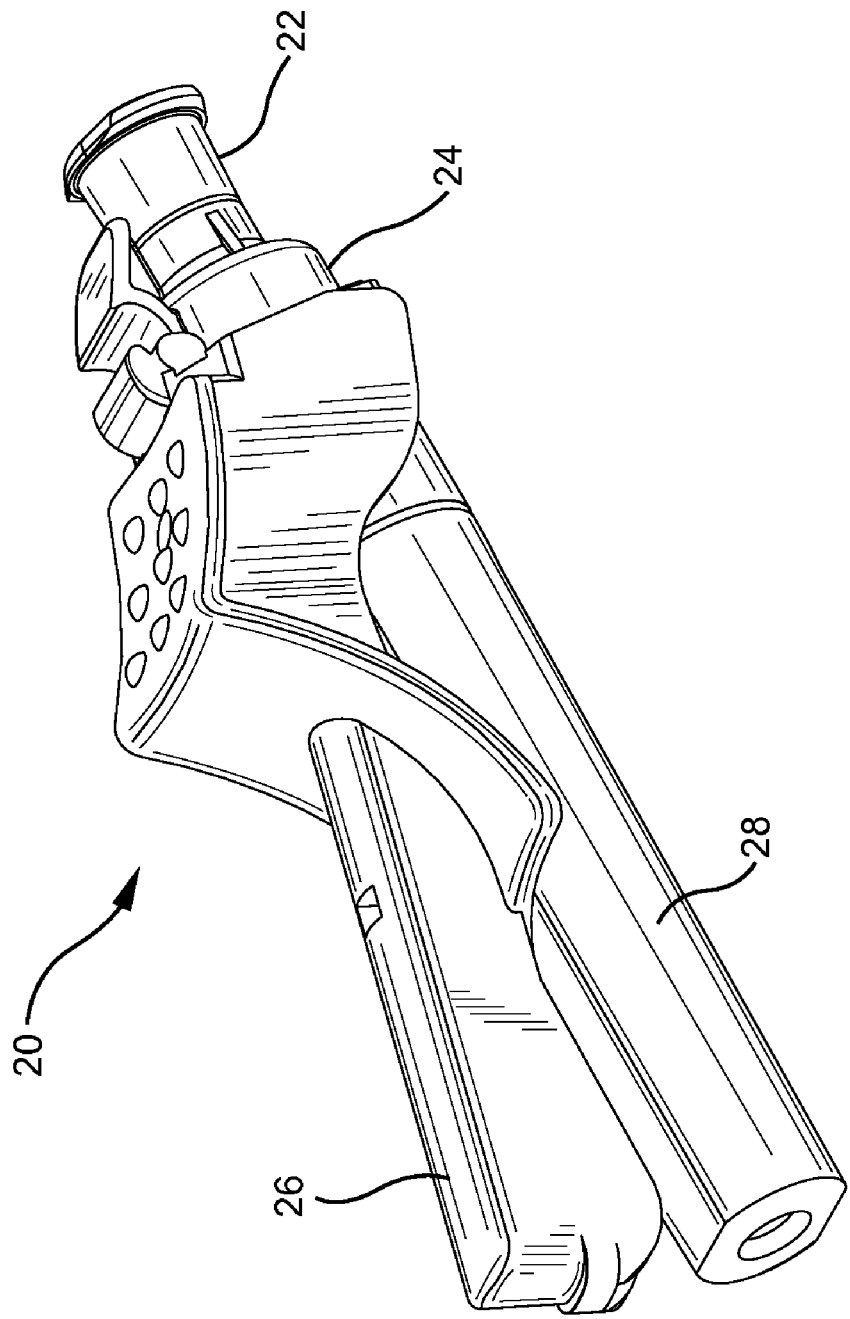
FIG. 1 is a top perspective view showing a needle shield assembly in accordance with a first embodiment of the invention.

While this invention is satisfied by embodiments in many different forms, there is shown in the drawings and herein described in detail, a preferred embodiment of the invention with the understanding that the present disclosure is to be considered exemplary of the principles of the invention and is not intended to limit the invention to the embodiment illustrated. The scope of the invention is measured by the appended claims and their equivalents.

Figure 2:
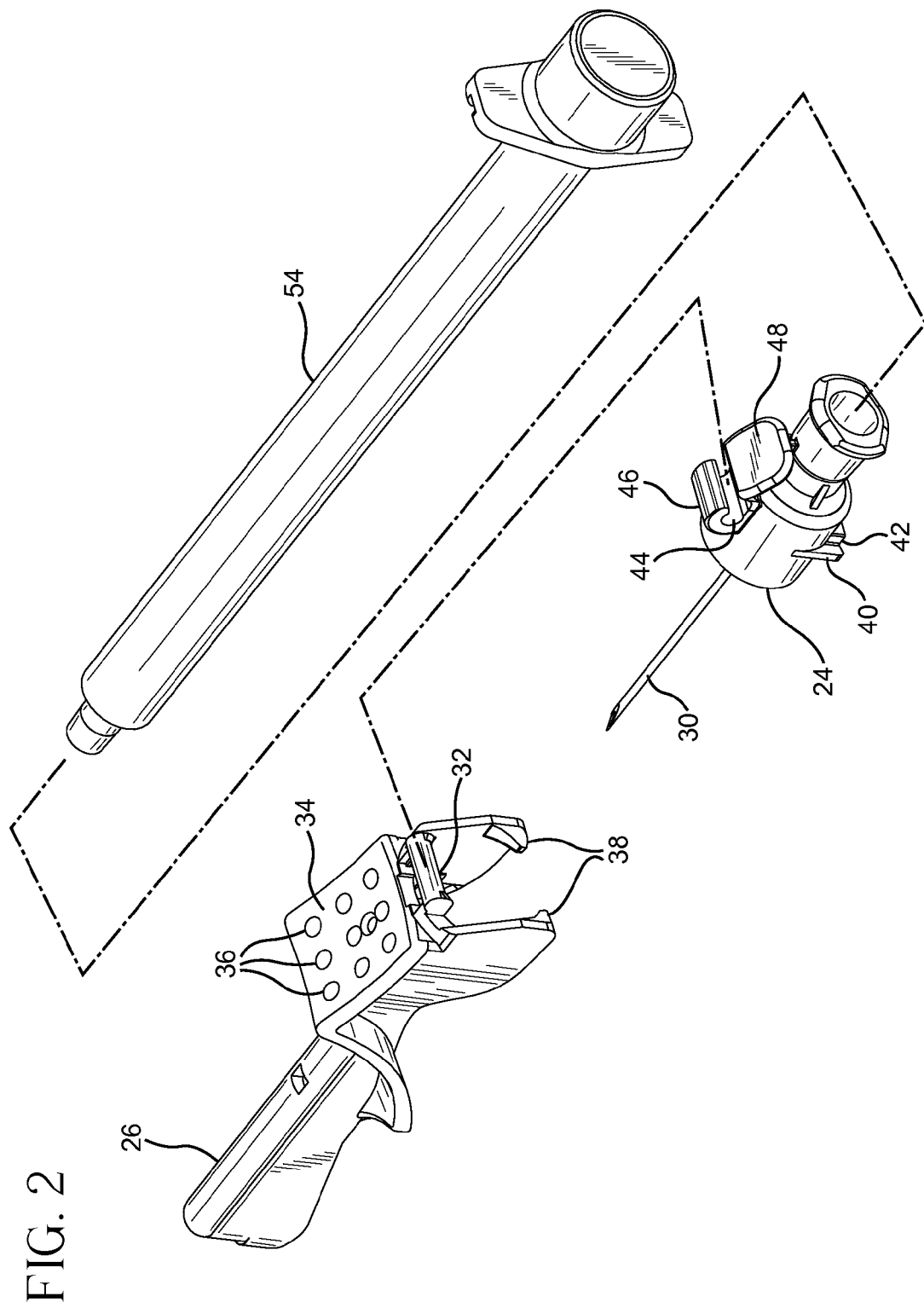
FIG. 2 is an exploded, top perspective view showing parts of the needle shield assembly in combination with a medical fluid delivery device.
Figure 3:
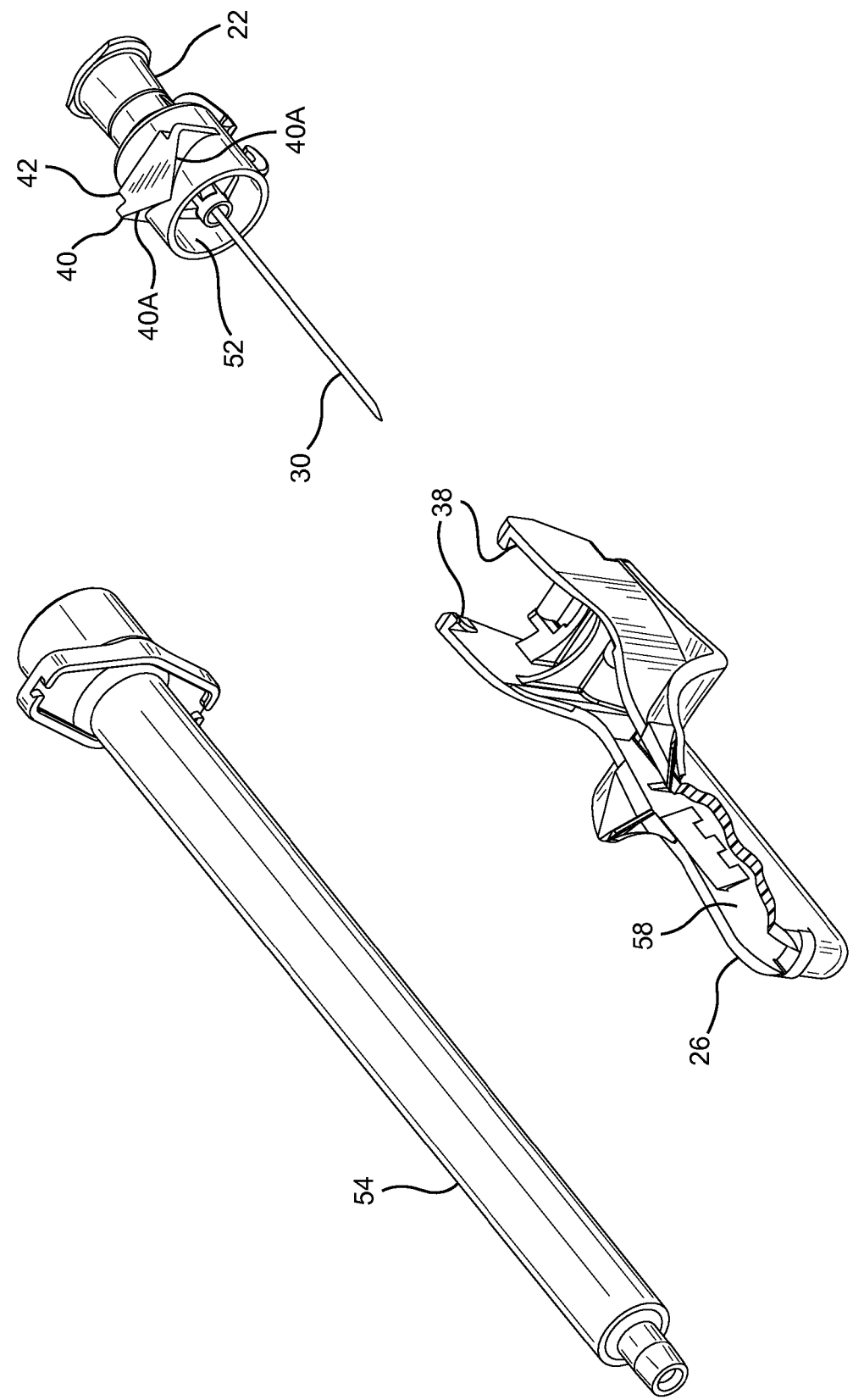
FIG. 3 is an exploded, bottom perspective view thereof.
Figure 4:
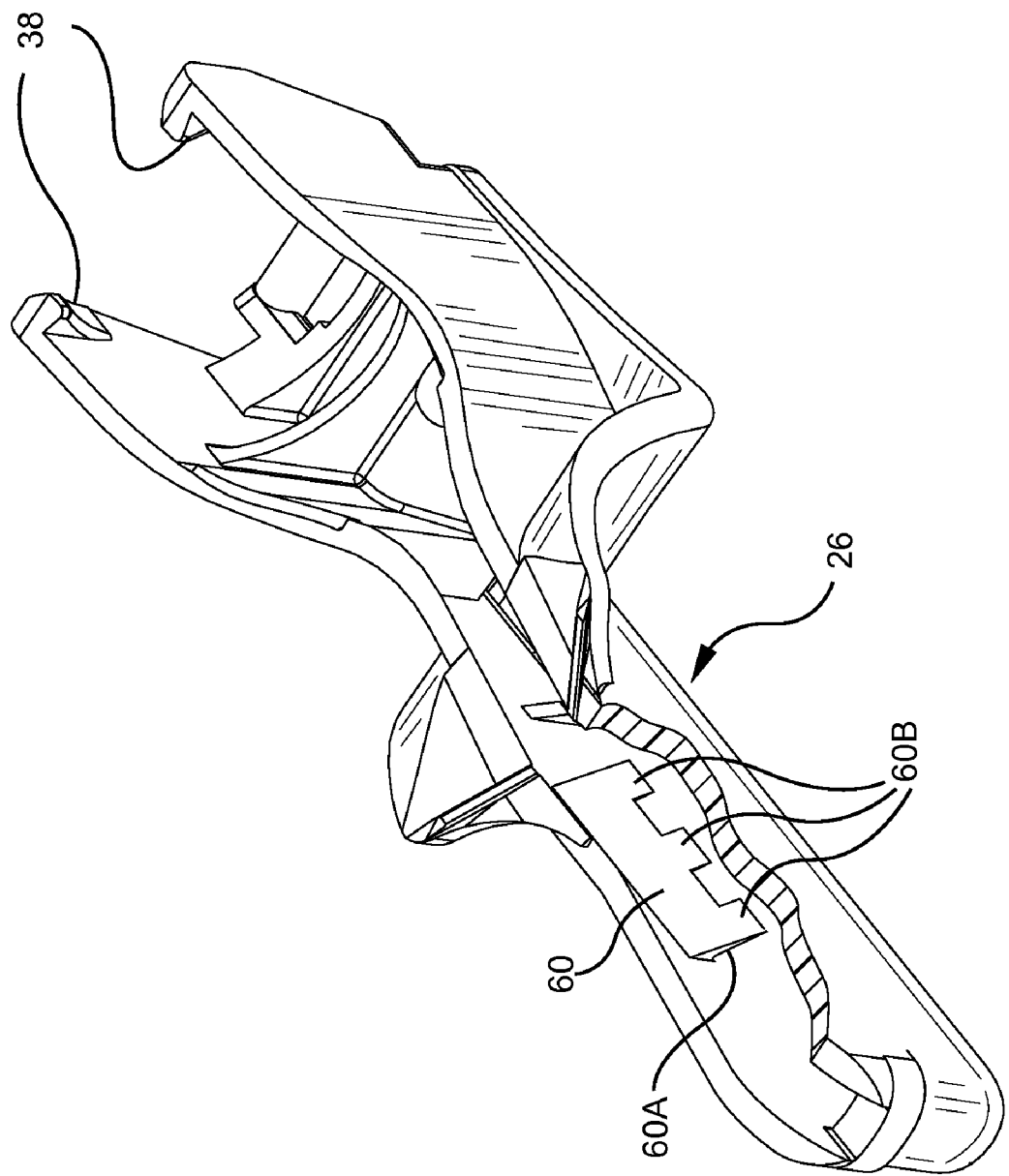
FIG. 4 is an enlarged, bottom perspective view showing the needle shield.

Referring to FIGS. 1 and 2, a needle shield assembly 20 is provided that includes a needle hub 22, a base member 24 connected to or integral with the needle hub, a needle shield 26, and a needle cover 28. The needle shield includes a proximal end portion that can be connected to the needle hub or base member, and a distal end portion that includes an elongate cavity for enveloping at least part of a needle cannula 30. The proximal end portion of the needle shield 26 includes an integral hinge pin 32 and a curved upper surface 34. The upper surface 34 is designed for engagement by a user's finger in order to pivot the needle shield about the hinge pin. Projections 36 may be provided on the curved upper surface. A pair of projections 38 extend inwardly from the proximal end of the needle shield. The needle cannula includes a proximal end 30A and a sharp distal end 30B. The proximal end thereof is secured to the needle hub 22 using adhesive such as epoxy or other appropriate means.

The base member 24 of the preferred embodiment includes a projection 40 having notches 42 for receiving the locking projections 38 at the proximal end of the needle shield 26. The projection 40 includes angled surfaces 40A that are engageable with the locking projections 38. The base member further includes a channel 44 having arcuate walls for receiving the hinge pin 32 on the needle shield. The channel 44 is positioned between a C-shaped projection 46 and a ramp 48. A cylindrical recess 52 in the base member is provided for receiving the proximal end of the needle cover.

The needle hub includes a proximal end 22A adapted for connection to a medical device such as a syringe 54. Various types of connectors are known and considered to be within the purview of the present invention. When secured to the medical device, fluid communication is established between the needle cannula 30 and the inner chamber 56 of the device. The distal end 22B of the hub is secured to the needle cannula 30.

Figure 5:
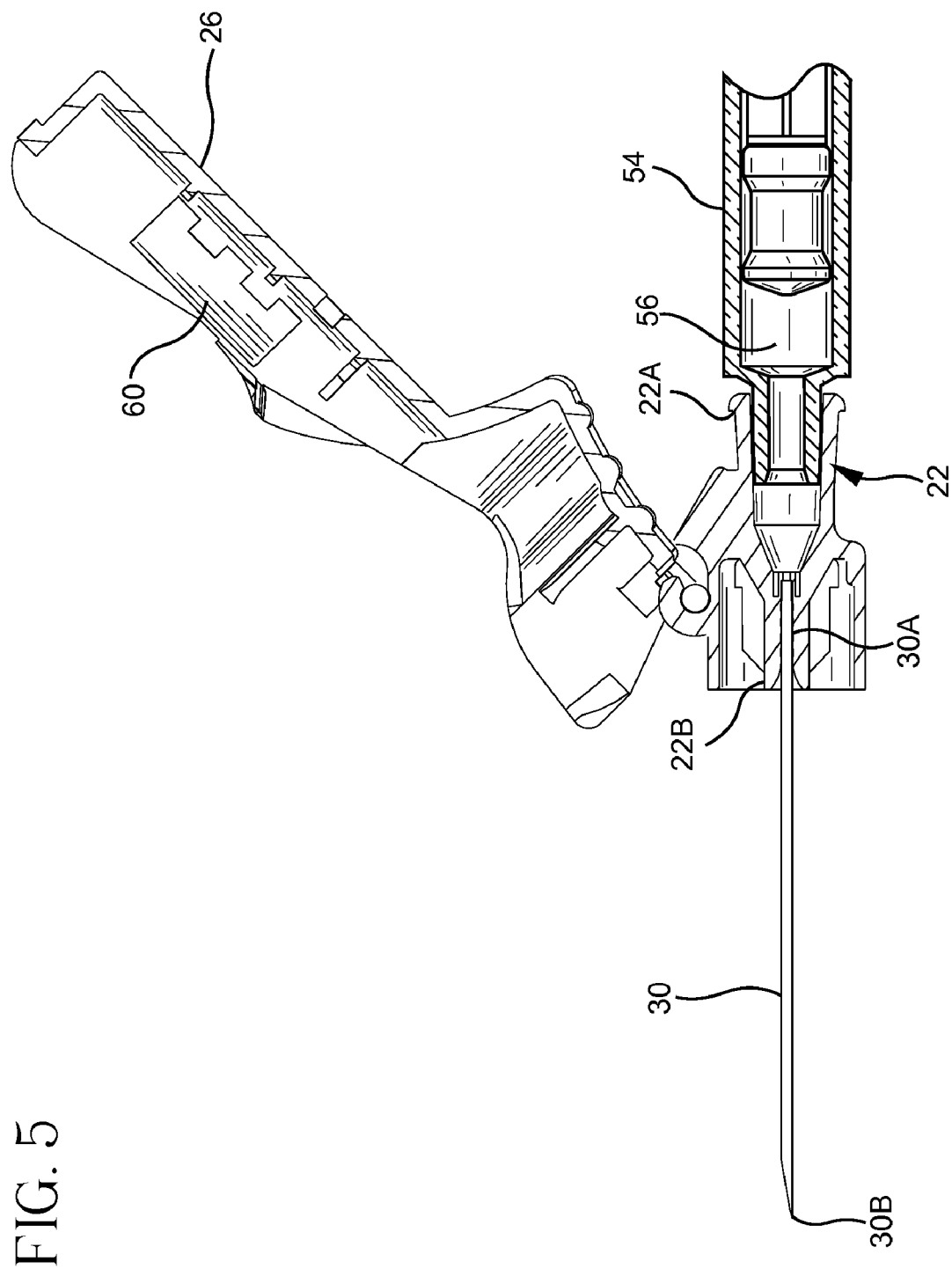
FIG. 5 is a sectional view of the needle shield assembly and the medical fluid delivery device showing the needle shield in a first position.
Figure 6:
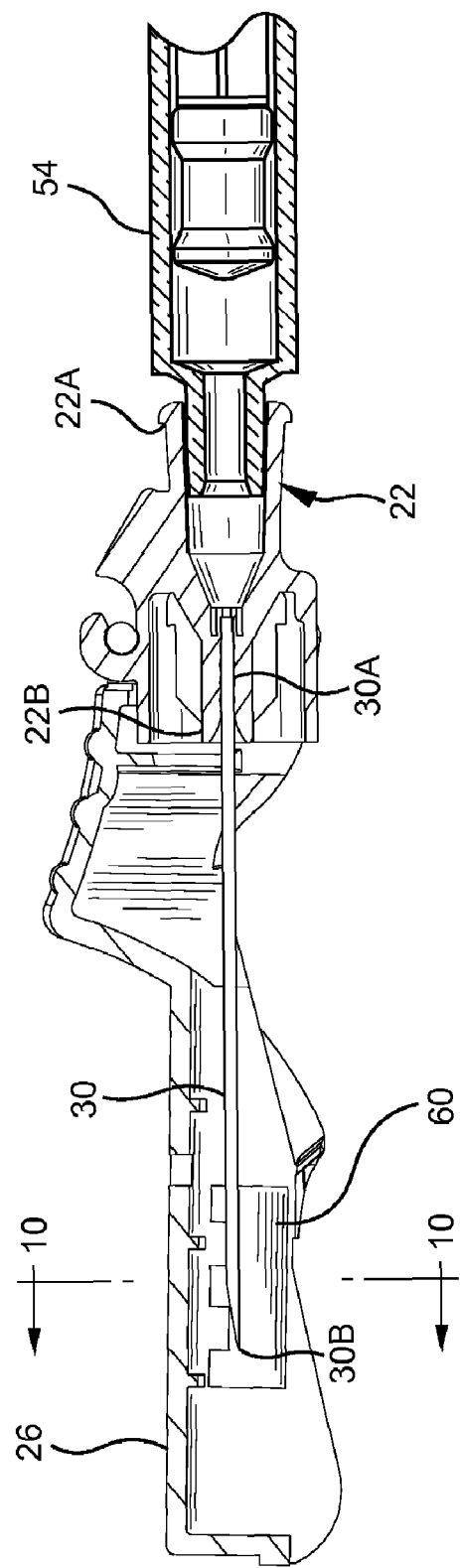
FIG. 6 is a sectional view thereof showing the needle shield pivoted towards a protective position covering the needle cannula.
Figure 7:
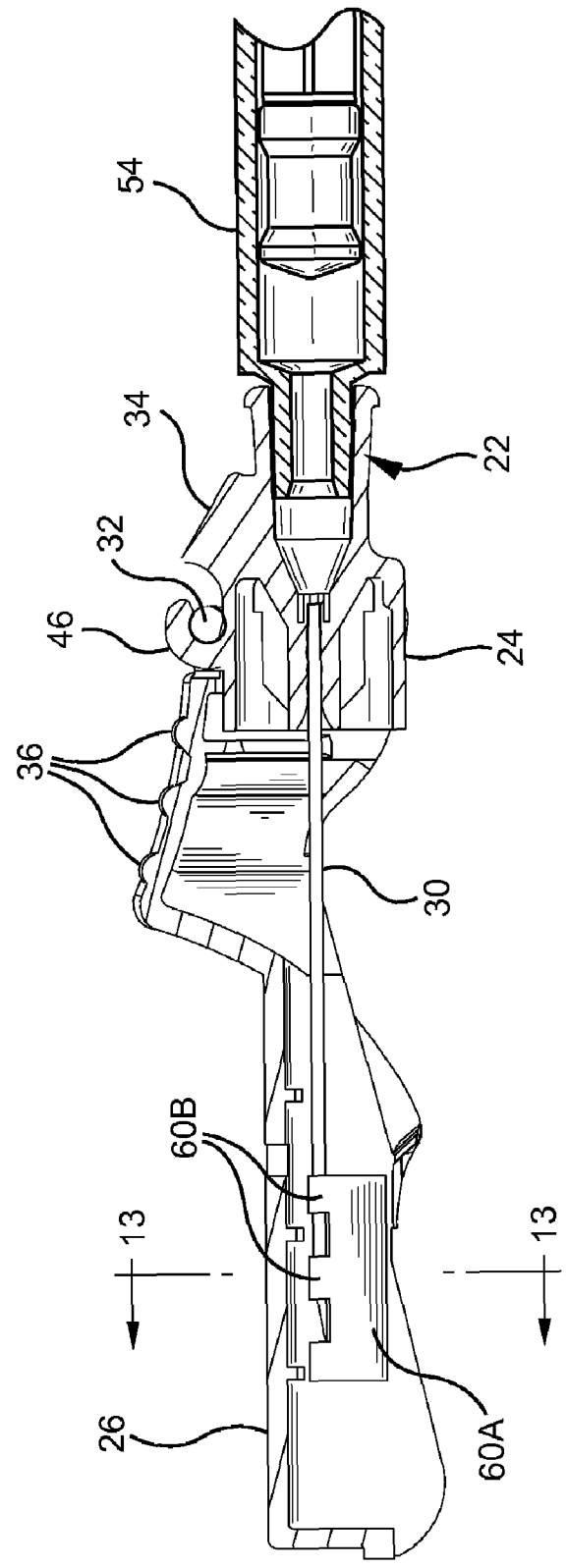
FIG. 7 is a sectional view thereof showing the needle shield in a protective position, the needle being trapped within the needle shield.
Figure 9:
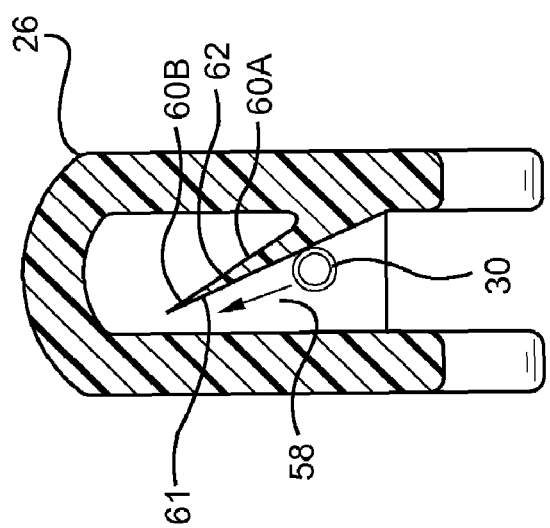
FIG. 9 is a sectional view of the needle cannula engaging a locking member in the needle shield.

The needle shield 26 can be pivoted about the hinge pin 32 between the open position shown in FIG. 5 and the closed position shown in FIG. 7. The needle cannula is entrapped with a cavity 58 defined by the needle shield 26 when the needle shield is in the closed position. One or more locking members 60 are provided for retaining the needle cannula in the needle shield. The needle shield 26 is further retained in the protective position by the movement of the projections 38 into the notches 42 in the base member 24.

Needle cannulas are available in many different lengths and gauges as they maybe used for different purposes. If the needle shield is to be locked in the protective position by the engagement of a deflectable locking member with the needle shaft, it is important that the locking member (or members) be sufficiently flexible that the needle is capable of temporarily displacing the locking member as it enters the needle shield cavity. The locking member must also exhibit sufficient rigidity to resist displacement so that the needle cannula, once entrapped, cannot easily be re-exposed by pivoting the needle shield and deflecting the locking member.

In accordance with a preferred embodiment of the invention, the locking member 60 is integral with a sidewall of the needle shield 26. These elements are preferably constructed from a semi-rigid plastic material such as polypropylene. The locking member includes a base portion 60A and three end portions 60B. It includes a tapered body that is thickest where it adjoins the wall of the needle shield. The base portion is relatively rigid and substantially more resistant to deflection than the end portions. This is due to several reasons, including the relative thickness of the two portions, the location of the base portion and the gaps between each of the end portions.

Figure 8:
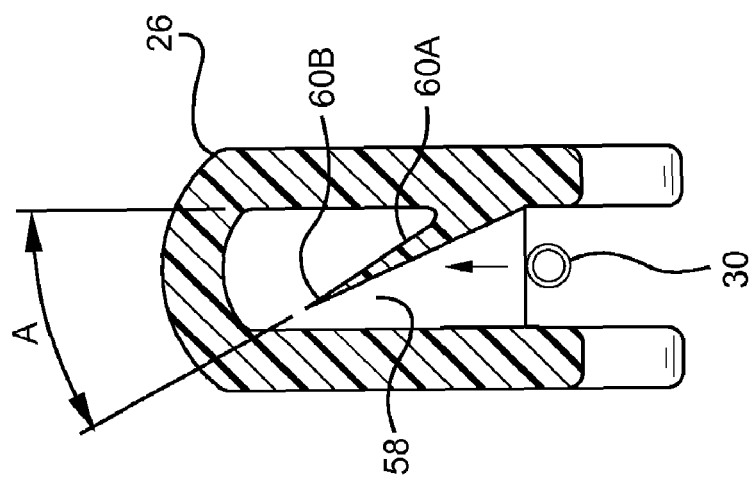
FIG. 8 is a sectional view of the needle shield showing a needle cannula entering the cavity in the needle shield.
Figure 11:
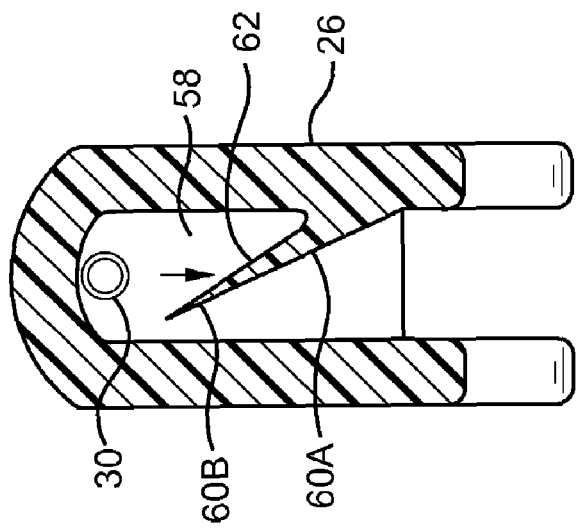
FIG. 11 is a sectional view of the needle cannula positioned behind the locking member.
Figure 10:
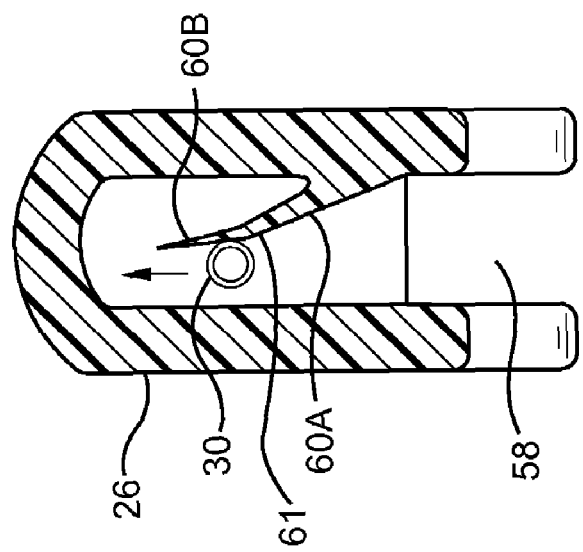
FIG. 10 is a sectional view thereof taken along line 10-10 of FIG. 6.
Figure 13:
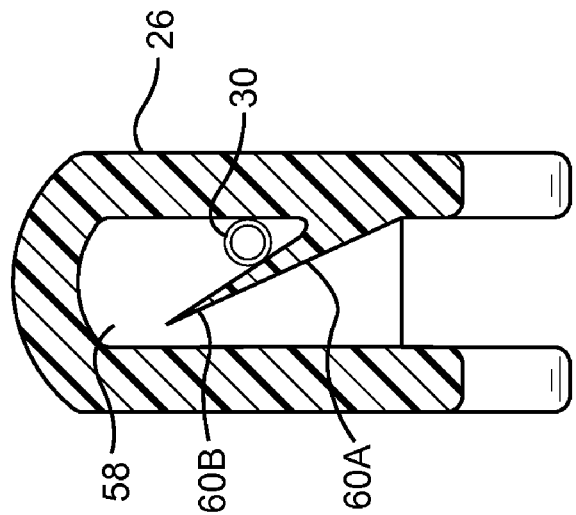
FIG. 13 is a sectional view taken along line 13-13 of FIG. 7.

FIGS. 8-13 show, in sequence, the needle cannula 30 entering the cavity 58 of the needle shield 26, becoming trapped within the shield, and engaging the locking member upon attempted pivoting of the needle shield 26 about the hinge pin from the needle cannula protective position. Referring first to FIG. 8, the needle cannula 30 is shown entering the cavity 58 of the needle shield as the needle shield is pivoted from the position shown in FIG. 5 to the protective position. The angular orientation of the locking member 60 away from the cavity opening is clearly shown. The locking member forms an angle A, as shown in FIG. 8, with the sidewall of the needle shield between about 20-70 degrees, and more preferably between 30-45 degrees. It also preferably extends over more than half the width of the cavity 58. Further rotation of the needle shield about the hinge pin 32 causes the needle cannula 30 to engage outer surface 61 of locking member 60, and preferably the relatively flexible end portions 60B of the locking member. It will be appreciated that a relatively long needle cannula may engage all three end portions 60B, while a shorter needle cannula may only engage one of them. Continued rotation of the needle shield causes the needle cannula to deflect flexible end portions 60B of the locking member relative to the base portion 60A, as shown in FIG. 10. The end portions 60B are preferably increasingly flexible from their connections to the base portion 60A to the tips thereof. The angular orientation of the locking member causes the needle cannula to be urged away from the side wall to which the locking member is attached and towards the tips of the end portions 60B as it moves into the cavity 58. A thicker (lower gauge) needle may deflect the end portions closer to the base portion 60A than a thinner (higher gauge) needle. Once the shaft of the needle cannula passes by the locking member 60, as shown in FIG. 11, the deflected end portion(s) 60B return substantially to their original position(s). The shaft of the needle cannula 30 is then blocked by the locking member 60. The locking projections 38 at the proximal end of the needle shield 26 simultaneously move into engagement with the projection 40 on the base member 24, further increasing the difficulty of re-exposing the needle.

Figure 12:
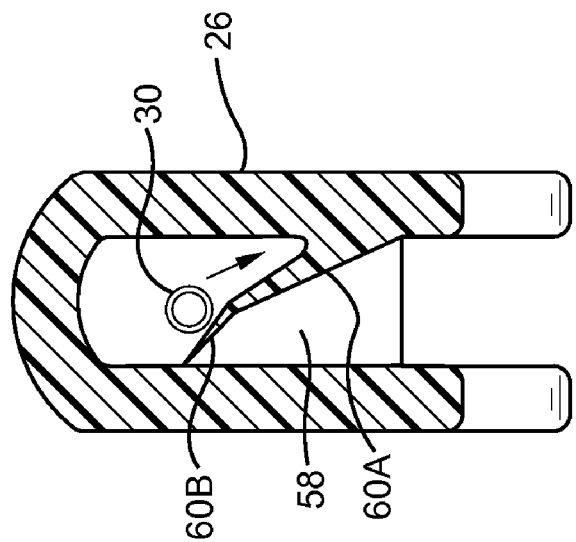
FIG. 12 is a sectional view showing movement of the needle with respect to the inner surface of the locking member.

Attempted rotation of the needle shield 26 away from the protective position causes the shaft of the needle cannula 30 to engage inner surface 62 of the locking member which, like the outer surface, is angled away from the opening to the needle shield cavity 58. Also, end portions 60B of the locking member are sized and shaped to deflect toward and contact the side wall of the cavity opposite the side wall connected to the base portion in response to contact with the needle cannula. Accordingly, if the needle cannula contacts the end portions 60B during an attempt to rotate the needle shield away from the protective position, the distal portions can deflect to contact the side wall, as shown in FIG. 12 thus preventing further deflection of the flexible distal portions that could allow the needle cannula to leave the shield and further urging the needle toward base portion 60A. Continued attempted rotation of the needle shield 26 causes the needle cannula to be directed towards the relatively rigid base portion 60A of the locking member, as shown in FIG. 12. As the locking member is substantially more difficult to deflect as the side wall of the needle shield is approached and the needle contacts base portion 60A, the needle cannula is highly unlikely to be re-exposed once trapped within the cavity 58. A substantially permanent locking of the needle cannula is accordingly achieved by the present invention.

It will be appreciated that various modifications could be made to the invention without departing from the spirit thereof. For example, the needle cannula, needle hub and adapter could be integral with the syringe instead of releasably coupled thereto. The locking member may be integral with the needle shield as shown, or be manufactured separately and then secured to the needle shield by an adhesive or mechanical fasteners. The end portion(s) of the locking member, which are integral with the base portion in the preferred embodiment, can be separate elements. One or more locking members may be employed within a needle shield. Each locking member may have one or a plurality of relatively flexible end portions that can be deflected relative to a relatively stiff base portion. The needle shield can be connected to the base member by a living hinge (not shown) or other suitable structure rather than through the use of a hinge pin.

The present invention provides a needle shield assembly that can be used to entrap relatively small diameter needles as well as those of larger diameter. The relatively flexible end portion(s) of the locking member can be designed to be deflected by small diameter needle cannulas that might otherwise be too flexible to deflect a locking element of uniform thickness or flexibility. Also, the ability of the end portions to contact the sidewall makes them relatively resistant to needle cannula leaving the cavity while being very flexible and able to allow the needle cannula to enter the cavity. The rigid base portion provides aggressive resistance to flexing even to forces that a large diameter needle cannula could apply. The relatively flexible end portion, acting as a cannula guide, directs the needle cannula towards the thicker, stronger base portion if one attempts to displace the needle shield. The same locking element will still have sufficient strength to substantially prevent the needle cannula from displacing the locking element once entrapped. The relative size and shape of the base portion and the end portions should be selected based on the length and diameter of the needle cannula being used with the needle shield.

What is claimed is:

1. A needle shield comprising:
   a proximal end portion including a connector;
   a distal end portion coupled to said proximal end portion and defining an elongate cavity for enveloping at least part of a needle cannula and said elongate cavity having an elongate cavity opening; and
   a needle cannula locking member coupled to said distal end portion and extending away from said elongate cavity opening and into said elongate cavity, said locking member including a relatively rigid base portion and a plurality of relatively flexible end portions, separated from each other by gaps, coupled to said base portion.

2. The needle shield of claim 1 wherein said base portion of said locking member is thicker than said end portions.

3. The needle shield of claim 1 wherein said locking member includes an outer surface facing said cavity opening and an inner surface, said inner and outer surfaces being substantially planar and extending away from said cavity opening.

4. The needle shield of claim 3 wherein said inner and outer surfaces converge to define a free end of said locking member.

5. The needle shield of claim 1 wherein said distal end portion includes a pair of opposing side walls, said base portion extending from one of said side walls and angled away from said elongate cavity opening.

6. The needle shield of claim 5 wherein said end portions are long enough to be flexed into contacting the side wall opposite said side wall from which the base portion extends.

7. A needle shield assembly comprising:
   a needle cannula having a proximal end, a distal end, and a lumen therethrough;
   a needle support, said needle cannula being connected to said needle support;
   a needle shield hingedly connected to said needle support, said needle shield including an elongate cavity, a pair of opposing side walls bordering said elongate cavity, and a cavity opening;
   a locking member connected to one of said side walls and extending into said elongate cavity away from said cavity opening, said locking member including inner and outer surfaces that converge in the direction away from said one of said side walls to which said locking member is connected, a base portion adjoining said one of said side walls, and an end portion adjoining said base portion, said end portion being relatively flexible with respect to said base portion;

said flexible end portion of said locking member being separated by gaps and deflectable with respect to said base portion by said needle cannula as said needle shield is moved towards a closed position to protect said needle cannula, said needle cannula being directed towards said one of said side walls by the inner surface of said locking member as said needle shield is moved towards an open position from the closed position.

8. The needle shield of claim 7 wherein said end portion is long enough to be flexed into contact with said side wall opposite said one of said side walls.

9. The needle shield assembly of claim 7 wherein said inner and outer surfaces of said locking member are substantially planar.

10. The needle shield assembly of claim 7 wherein said locking member forms an angle with said one of said side walls between about 20-70 degrees.

11. The needle shield assembly of claim 10 wherein said angle is between about 30-45 degrees.

12. The needle shield assembly of claim 7 wherein said locking member includes a plurality of flexible end portions extending from said base portion.

13. A medical device comprising:
a vessel having a first end and a second end;
a needle cannula having a proximal end, a distal end, and a lumen therethrough, said needle cannula being connected to said first end of said vessel;
a needle shield pivotably coupled to said vessel, said needle shield including first and second opposing side walls, a cavity between said side walls for receiving at least part of said needle cannula, and a cavity opening, said needle shield being pivotable between an open position where at least the distal end of said needle cannula is exposed and a closed position where at least the distal end of said needle cannula is positioned within said cavity;
a locking member connected to said first side wall of said needle shield and extending away from said opening and into said cavity, said locking member including a relatively rigid base portion adjoining said first side wall and a plurality of relatively flexible end portions separated by gaps extending from said base portion and defining a free end;
said locking member being positioned such that said needle cannula contacts and displaces said relatively flexible end portion upon movement of said needle shield into said closed position;
said locking member including an outer surface opposing said cavity opening and an inner surface extending at an acute angle with respect to said first side wall such that when said needle shield is moved from said closed position towards said open position, said needle cannula is urged by said inner surface of said locking member towards said first side wall.

14. The medical device of claim 13 wherein said inner and outer surfaces of said locking member converge between said first sidewall and said free end.

15. The medical device of claim 13 wherein said acute angle is between about 30-45 degrees.

16. The medical device of claim 13 wherein said vessel is a syringe barrel.

17. The medical device of claim 16 further including a needle support secured to said syringe barrel, and said needle shield being connected to said needle support by a hinge.

18. The medical device of claim 13 wherein said inner surface of said locking member is substantially planar.

19. The medical device of claim 13 wherein said end portion is long enough to be flexed so that said free end contacts said second side wall.

* * * * *